United States Patent
Scholten et al.

(10) Patent No.: US 8,986,256 B2
(45) Date of Patent: Mar. 24, 2015

(54) MANUFACTURING METHOD FOR A POROUS MICRONEEDLE ARRAY AND CORRESPONDING POROUS MICRONEEDLE ARRAY AND CORRESPONDING SUBSTRATE COMPOSITE

(75) Inventors: Dick Scholten, Stuttgart (DE); Michael Stumber, Korntal-Muenchingen (DE); Franz Laermer, Weil der Stadt (DE); Ando Feyh, Palo Alto, CA (US)

(73) Assignee: Robert Bosch GmbH, Stuttgart (DE)

( * ) Notice: Subject to any disclaimer, the term of this patent is extended or adjusted under 35 U.S.C. 154(b) by 408 days.

(21) Appl. No.: 12/925,804

(22) Filed: Oct. 29, 2010

(65) Prior Publication Data

US 2011/0137254 A1   Jun. 9, 2011

(30) Foreign Application Priority Data

Nov. 10, 2009   (DE) .......................... 10 2009 046 581

(51) Int. Cl.
*A61M 5/00* (2006.01)
*A61M 37/00* (2006.01)
*B81C 1/00* (2006.01)

(52) U.S. Cl.
CPC ........ *A61M 37/0015* (2013.01); *B81C 1/00111* (2013.01); *A61M 2037/0053* (2013.01); *B81B 2201/055* (2013.01); *B81B 2203/0361* (2013.01); *B81C 2201/0114* (2013.01); *B81C 2201/0115* (2013.01); *B81C 2203/0118* (2013.01); *B81C 2203/054* (2013.01)
USPC .......................................... 604/173; 438/113

(58) Field of Classification Search
CPC .............. A61M 2037/0023; A61M 2037/0053
USPC ........................................... 604/173; 438/113
See application file for complete search history.

(56) References Cited

U.S. PATENT DOCUMENTS

| | | | |
|---|---|---|---|
| 6,537,242 B1* | 3/2003 | Palmer ............................ | 604/22 |
| 2003/0135161 A1 | 7/2003 | Fleming | |
| 2003/0199812 A1* | 10/2003 | Rosenberg ....................... | 604/47 |
| 2006/0047243 A1 | 3/2006 | Rosenberg | |
| 2009/0200262 A1 | 8/2009 | Scholten et al. | |
| 2009/0301994 A1* | 12/2009 | Bhandari et al. ................ | 216/11 |
| 2010/0268200 A1* | 10/2010 | Banister et al. ............ | 604/891.1 |

FOREIGN PATENT DOCUMENTS

| | | |
|---|---|---|
| CN | 1199920 | 11/1998 |
| CN | 1986001 | 6/2007 |
| CN | 100998901 | 7/2007 |
| DE | 10 2006 028 781 | 12/2007 |

* cited by examiner

*Primary Examiner* — Emily Schmidt
(74) *Attorney, Agent, or Firm* — Kenyon & Kenyon LLP

(57) ABSTRACT

A manufacturing method for a porous microneedle array includes: forming a plurality of porous microneedle arrays, each having at least one microneedle and a porous carrier zone lying beneath it on the face of a semiconductor substrate; forming an interlayer between a non-porous residual layer of the semiconductor substrate located on the back side of the semiconductor substrate and the carrier zone, which has greater porosity than the carrier zone; detaching the residual layer from the carrier zone by breaking up the interlayer; and separating the microneedle arrays into corresponding chips.

10 Claims, 2 Drawing Sheets

MANUFACTURING METHOD FOR A POROUS MICRONEEDLE ARRAY AND CORRESPONDING POROUS MICRONEEDLE ARRAY AND CORRESPONDING SUBSTRATE COMPOSITE

BACKGROUND OF THE INVENTION

1. Field of the Invention

The present invention relates to a manufacturing method for a porous microneedle array and a corresponding porous microneedle array and a corresponding substrate composite.

2. Description of Related Art

Although applicable to any micromechanical components, the present invention and the related background on which it is based will be explained with regard to micromechanical components in silicon technology.

Porous microneedle arrays, which are made for example of porous silicon, are used in the area of transdermal drug delivery as an extension of medicinal patches, as carriers of a vaccine or also for removing body fluid (so-called transdermal fluid) for the diagnosis and analysis of body parameters (such as glucose, lactate, alcohol, etc.).

Medicinal patches (transdermal patches) for small molecules (such as nicotine) are widely known. The range of utilization is normally limited to small molecules that are easily able to pass through the skin. In order to expand the range of use of such transdermal applications to other active agents, so-called chemical enhancers or various physical methods (ultrasound, heat pulses) are used, which help to defeat the protective layer of the skin even for larger agent molecules.

Another method for doing this is mechanical penetration of the outer layers of the skin (stratum corneum) by fine, porous microneedles combined with the administration of an active agent, preferably using a patch containing an active agent, into which the microneedles may already be integrated, or using a metering device which enables targeted dispensation (bolus, pause, increase, etc.) of active agents.

Published German patent application document DE 10 2006 028 781 A1 discloses a method for manufacturing porous microneedles, arranged in an array on a silicon substrate, for transdermal administration of medications. The method includes forming a microneedle array having a plurality of microneedles on the face of a semiconductor substrate, which rise above a carrier zone of the semiconductor substrate, as well as partial porosification of the semiconductor substrate to form porous microneedles, the porosification starting from the face of the semiconductor substrate and a porous reservoir being formed in the interior of the structures.

Another method for manufacturing a porous microneedle array is known from published Chinese patent application document CN 100998901A.

The previously known approaches provide for manufacturing porous microneedle arrays on the wafer face using known plasma etching techniques. After the microneedle arrays have been manufactured, the wafer is anodized electrochemically in aqueous hydrofluoric acid by applying electrical potentials, whereby the material silicon is transformed into porous silicon starting from the wafer face having the microneedle array. This porosification cannot proceed extensively throughout the entire wafer, however, because the first pore that reaches the back of the wafer forms an electrical short circuit or bypass around the wafer, so that further anodization is slowed or comes to a stop after a certain time. Moreover, it is very time-consuming and uneconomical, or even impossible, to anodize through an entire wafer thickness, or even only several hundred µm of a wafer thickness.

For that reason, use is often made in the related art of so-called ablating processes, in which the wafer is thinned to a lesser wafer thickness prior to anodizing, for example by mechanical grinding or chemical wet etching or plasma etching in the gaseous phase. That shortens the time needed for through-porosification of the wafer thanks to its reduced thickness, although at the cost of an increased risk of breaking during this process or other subsequent processes.

Furthermore, it remains impossible, even with a thinned wafer, to anodize the latter over its complete extent through the entire remaining wafer thickness, due to the previously mentioned electrical bypass problem through the first pores that extend all the way through the wafer.

For this reason, for example, metal layers and/or metal foils are applied to the back of the wafer, which may be removed again after the anodizing is completed. It is also possible to anodize the wafer only partially, either until the first pores reach the back, but most of the pores have not yet gotten that far, or right from the outset to anodize only to a certain preselected depth in the silicon bulk material. In both cases, material is next ablated mechanically or chemically from the back of the wafer until a completely porous structure that extends through the remainder of the wafer is achieved. Another positive effect achieved with the ablation is that the remaining silicon is significantly thinner than that of the initial wafer, which makes it easier for active agents to pass through into the skin or for transdermal fluid to pass out of the skin, in one direction and in the other direction.

With these grinding or etching procedures, however, there is great expense, mechanical stress on the wafer, a risk of breaking, and a need to protect the microneedle array present on the face from mechanical damage. Since silicon is a brittle and breakable material, there is a risk of damage when handling the front of the wafer, as is necessary for example when grinding the back of the wafer. However, temporary protective measures during the process mean an additional, sometimes substantial, processing expense.

BRIEF SUMMARY OF THE INVENTION

The manufacturing method for a porous microneedle array according to the present invention and the corresponding porous microneedle array and the corresponding substrate composite have the advantage that it is easily possible to remove a non-porous remaining layer of the semiconductor substrate from the carrier zone and the microneedles provided thereon.

The idea underlying the present invention is to form an interlayer between a non-porous remaining layer of the semiconductor substrate present on the back side of the semiconductor substrate and the carrier zone, the interlayer having a greater porosity than the carrier zone.

According to a preferred refinement, a plastic cap substrate is applied on the face of the semiconductor substrate over the microneedle arrays, prior to the detachment and separation.

The plastic cap substrate preferably has flanges and/or recesses, which interact with the edges to position the plastic cap substrate. During separation, protective covers sawn out of the cap may remain on the chips.

This permits safe handling, safety during further assembly measures, and integration into a patch containing an active agent or into a measuring device, or even subsequent transport, packaging and the commercial logistics. It is particularly preferable if the protective caps are not removed until as late as possible, ideally immediately before the microneedle arrays are put to use by the customer, in order to guarantee optimal protection from damage, soiling and infectious germs until then.

DETAILED DESCRIPTION OF THE INVENTION

Figure 1A:
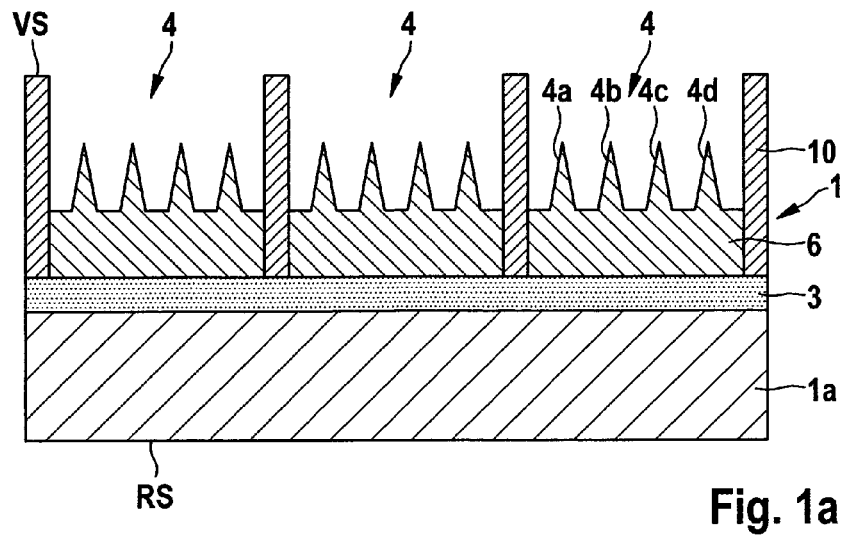
FIGS. 1a through 1d show schematic cross-sectional views illustrating an example embodiment of the manufacturing method according to the present invention for a porous microneedle array.

In the figures, like reference numerals designate the same or functionally equivalent elements.

FIGS. 1a through 1d show schematic cross-sectional views illustrating an example embodiment of the manufacturing method according to the present invention for a porous microneedle array.

In FIG. 1, reference numeral 1 designates a semiconductor substrate of silicon in the form of a silicon wafer.

To reach the process state shown in FIG. 1a, porous microneedle arrays 4, each having a plurality of microneedles 4a, 4b, 4c, 4d, are etched into face VS of semiconductor substrate 1, using plasma technology in a known manner. After the etching process, known for example from EP 0 725 285 B1, edges 10 of the individual microneedle arrays 4 remain, which are higher than the microneedles 4a, 4b, 4c, 4d of microneedle arrays 4 themselves.

In the known method, periodic columns are etched into face VS of semiconductor substrate 1 using an etching process that is not strictly anisotropic, so that undercuts of the structures defined by the mask occur. The spatial convergence of the so-called "bow profiles" during the etching results in the undercuts and the formation of apices at the points of convergence. As a result of these undercuts, an upper part and a lower part of the columns are separated from each other, forming the apices. The upper part of the former columns still holds firmly on the outside to the chip edge, and may be broken off of this chip edge (for example by using adhesive films, which are first applied and later are pulled off again). When this is done, the upper parts of the former columns remain stuck to the film, after which only microneedles 4a, 4b, 4c, 4d of microneedle arrays 4 remain sunk in their respective edges.

This is followed by an electrochemical anodization process in an electrolyte containing hydrofluoric acid. In a known manner and in a known apparatus, this transforms the silicon material of face VS of semiconductor substrate 1 into porous silicon by passing an electric current through semiconductor substrate 1. This anodization process is continued until a desired thickness of the porous silicon layer has been produced on face VS of semiconductor substrate 1, i.e., so that the porosification of microneedles 4a, 4b, 4c, 4d is complete, and furthermore a desired depth of a porous carrier zone 6 lying beneath microneedles 4a, 4b, 4c, 4d has been achieved. The porosity of microneedles 4a, 4b, 4c, 4d and of carrier zone 6 is chosen low enough, through the current density and hydrofluoric acid concentration, so that adequate stability of microneedle arrays 4 and of carrier zone 6 results.

Next the current density is temporarily increased to such an extent or the hydrofluoric acid concentration is reduced to such an extent, or a combination of both measures is chosen, that an additional unstable interlayer 3 is formed between a non-porous residual layer 1a of semiconductor substrate 1 present on back side RS of the semiconductor substrate and carrier zone 6, which interlayer has greater porosity than carrier zone 6. This unstable interlayer 3 of highly porous material may easily be broken up later to separate residual layer 1a from carrier zone 6.

It is also possible to force the current density into the range of so-called electropolishing, so that beneath carrier zone 6, which has comparatively low porosity, the silicon is completely dissolved and a regular hollow structure is formed as interlayer 3.

This is followed by cleaning and hydrophilization of porous functional structures 4, 6. Cleaning is important for removing all remnants of hydrofluoric acid residue. It may be performed, for example, using water-alcohol mixtures. The subsequent hydrophilization causes porous functional structure 4, 6 when in use to eagerly absorb fluids, such as active agent solutions or transdermal fluids, to become quite saturated with them, and also to let them pass quickly. Oxidizing wet chemistries in the form of aqueous solutions may be used for this, such as peroxides, hypochlorite, chlorite, chlorates or perchlorates, concentrated sulfuric acid, etc., or combinations of the above. In addition, oxygen plasmas or ozone-containing gases, either dry or dissolved in aqueous liquids or in combination with water vapor, may be employed for the hydrophilization of the internal silicon surfaces. It is also possible to achieve a hydrophilization of the internal structure of the porous silicon by thermal oxidation or preoxidation in an oxidizing atmosphere of, for example, oxygen, water vapor, or other oxidizing gases at an elevated temperature. Such thermal processes are also easily possible with the present wafer state according to FIG. 1a.

Figure 1B:
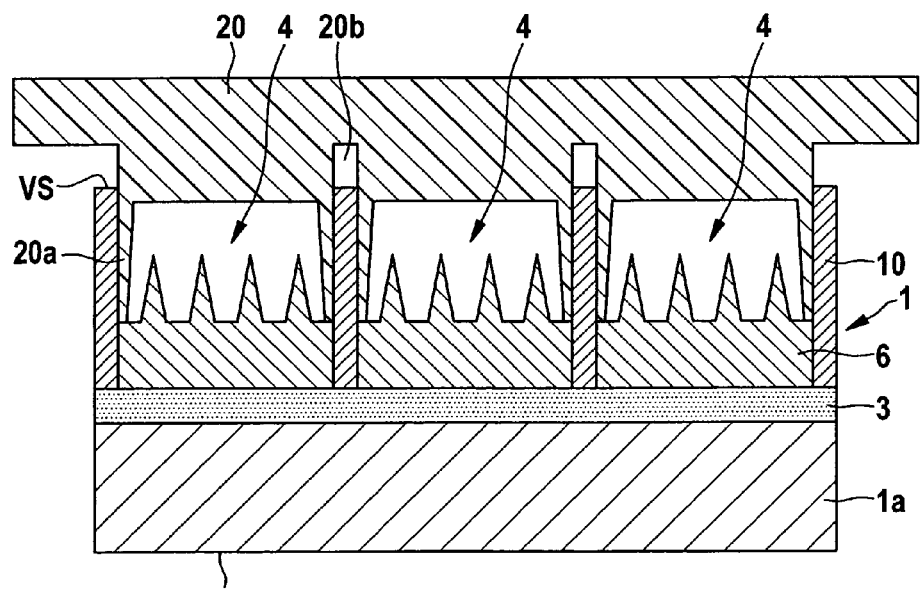

In addition, referring to FIG. 1b, immediately before interlayer 3 is broken up, a prestructured plastic substrate 20 in wafer form is bonded or cemented to semiconductor substrate 1, which carries microneedle arrays 4 and is partially porous. This plastic wafer 20 may be manufactured from known plastics, for example by injection molding processes and/or hot embossing processes. Its contour must be matched to the topography of microneedle arrays 4. In particular, edges 10 may be used for self-adjustment, by forming corresponding counterstructures in the form of columns 20a and/or recesses 20b in plastic wafer 20, into which edges 10 easily snap before plastic wafer 20 is cemented to semiconductor substrate 1. This saves a more expensive adjustment of semiconductor substrate 1 and plastic wafer 20, and ensures that both parts may nevertheless be fitted together precisely. FIG. 1b depicts the process status after cementing.

Figure 1C:
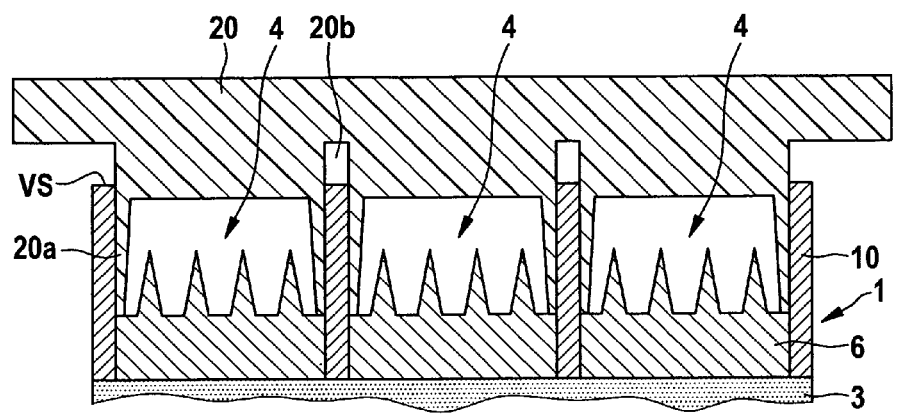

Additionally, referring to FIG. 1c, interlayer 3 is broken up in order to separate residual layer 1a from carrier zone 6. This may be done mechanically by tearing or forcing in a blade or a separator, or using a thread or thin wire that is drawn through interlayer 3. After this, a stable system of carrier zone 6, edges 10, microneedle arrays 4 and plastic cap wafer 20 is obtained. Afterward the remains of interlayer 3 may be removed mechanically or chemically. For certain applications they may also be preserved, however, for example in combination with a patch containing active agents, where remnants of the interlayer are not a problem or may be desired, for example as a reservoir.

Figure 1D:
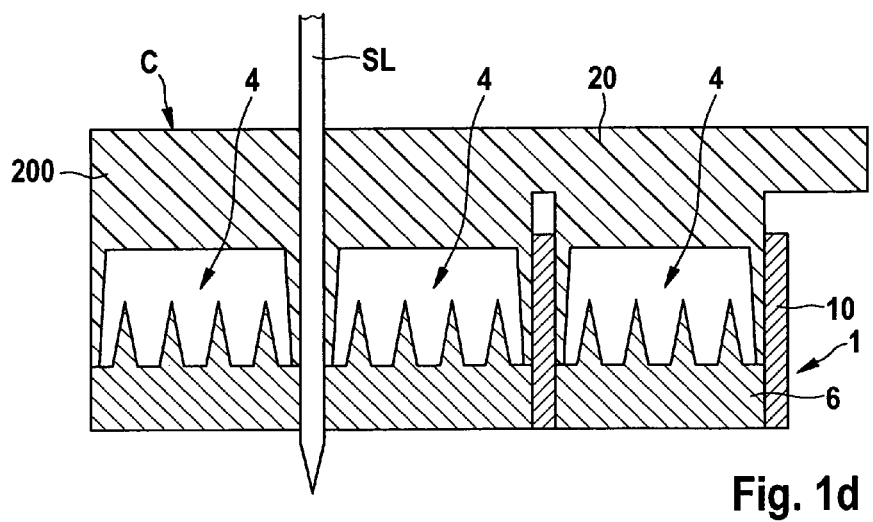

Finally, referring to FIG. 1d, the wafer composite is sawn along edges 10 in sawing lines SL, in order to separate microneedle arrays 4 thereby into corresponding chips C. The sawing causes edges 10 to disappear completely. In this way individual chips C are obtained, each having a microneedle array 4 under its own protective cap 200, microneedles 4a, 4b, 4c, 4d of microneedle arrays 4 being the highest elevations on the silicon face, thanks to the removal of chip edge 10, which is a prerequisite for sticking into the skin in the later application.

The advantages of the manufacturing method according to the present specific embodiment are, on the one hand, that fully porosified microneedle arrays 4 on thinned carrier zones 6 may be obtained thereby in a very simple process. No grinding processes are needed for thinning pre-processed wafers, with all the attendant problems and risks, such as mechanical damage to microneedles 4a, 4b, 4c, 4d. Instead, only exactly the wafer thickness that is actually later needed is porosified, which prevents wasteful through-wafer processing. The altogether relatively thin porous silicon structure is also particularly favorable because a thin structure permits a rapid substance exchange between the front and back, i.e., in the case of a patch containing active agents, a flow of agents from an agent reservoir through porous carrier zone 6 and porous microneedles 4a, 4b, 4c, 4d under the skin, or in the case of a diagnostic application, the flow of the transdermal fluid via porous microneedles 4a, 4b, 4c, 4d through porous carrier zone 6 to a measuring system of whatever type. Moreover, a thinner carrier zone 6 is more flexible and less at risk of breaking when bent than a thick, rigid carrier zone.

The linking to a plastic wafer 20 in the process ensures strength and even permits particularly thin carrier zones, i.e., for example, less than 100 μm thick. Before the porous surface having microneedles 4a, 4b, 4c, 4d is detached the structure is relatively strong, because it is anchored on the substrate wafer via highly porous interlayer 3. After the non-porous residual layer of semiconductor 1 is detached by means of highly porous interlayer 3, the strength continues to be guaranteed by plastic wafer 20. After sawing, one has small and relatively flexible chips C, which remain stabilized by plastic cap 200. Often additional carriers are found in the later applications, such as a patch containing active agents or an agent reservoir or a massive carrier of a measuring system of whatever type, to which the microneedle arrays of systems 4 are attached.

In a procedural variant (not depicted in the drawing), the saw step is preferred along sawing lines SL, prior to the breakup of interlayer 3. To this end, the sawing process should advantageously not cut through the entire substrate wafer thickness, but rather the cuts should essentially be certain to reach highly porous interlayer 3 or essentially cut through it reliably. The depth to which the cut is actually executed depends on the desired residual strength of semiconductor substrate 1. The deeper the cuts, the more fragile the semiconductor substrate, and the greater the effort and cost of holding and stabilizing to prevent breaking during subsequent processing.

Next, after the pre-sawing to a predetermined depth which is less than the thickness of semiconductor substrate 1, individual chips 10 having a microneedle array 4 may be picked off of the porous remaining layer of semiconductor substrate 1. For example, a pick-and-placer is able to grasp the sawn-through individual caps and/or chips C lying beneath them and tear them out of semiconductor substrate 1 mechanically, the detachment being very easily possible thanks to the highly porous and unstable interlayer 3. Individual chips C detached from semiconductor substrate 1 may then be stockpiled elsewhere by the pick-and-placer for further processing, or may be placed or cemented onto a different carrier.

In addition, the manufacturing process using plastic cap wafers 20 includes stabilization and protection of the sensitive microneedle arrays 4 on wafer face VS during the critical manufacturing phase of separation from substrate 1, and particularly during the sawing. In the process phases in which microneedle arrays 4 are still recessed relative to the chip edges, a certain protection of microneedle arrays 4 is ensured anyway, since they are set back spatially. Microneedles of brittle silicon are generally sensitive to mechanical influences, since these may damage the tips or even break off whole needles. It is therefore advantageous for the microneedles to be protected from mechanical influences as early as possible and as long as possible in the subsequent workflow by a protective structure such as the described plastic caps 200. Sawing is a very critical process here, which places severe mechanical strains on the structures. It is particularly beneficial here that sawing water, sawing slurry and particles may be kept away from the sensitive microneedle arrays 4 thanks to plastic caps 200. An additional advantage is that sawing removes the interfering (because elevated) chip edges, which would hinder later insertion of the microneedle arrays into the skin.

Even after sawing, it is beneficial for protective caps 200 to remain on microneedle arrays 4. This permits safe handling, safety during further assembly measures, and integration into a patch containing an active agent or into a measuring device, or even during subsequent transport, packaging and the commercial logistics. It is particularly preferable if the protective caps are not removed until as late as possible, ideally immediately before the microneedle arrays 4 are put to use by the customer, in order to guarantee optimal protection from damage, soiling and infectious germs until then. In particular, the sterility of microneedle arrays 4 may be guaranteed thereby, since contact with the needles themselves is impossible thanks to the caps. In the case of a patch application, protective cap 200 may be torn off at the same time, for example when the patch packaging is opened, for example by pulling off a sealing film from the inner side of the patch. In the case of an application in a measuring system such as a combination solution with a glucose test strip, the protective cap may also be torn off or pried off by the customer, for example immediately before the microneedles are inserted into the skin. Up to this point in time the structures are safely kept under their caps 200 and thus continue to be protected from foreign influences and contamination or germs, and their sterility is ensured.

Another advantage is the fact that the back side of chips C with porous microneedle arrays 4 is not flat, but rather the topography of face VS of semiconductor substrate 1 having the microneedles is reflected there. Indentations on the face result in corresponding elevations on back side RS. Elevations on the face of the wafer correspond to indentations or grooves on back side RS. This topography of back side RS permits air displaced from the porous structure to escape into or via the indentations, for example if the porous structure starting from the microneedle arrays of face VS becomes saturated with transdermal fluid from beneath the surface of the skin, as may be the case in a measuring application.

Preferred applications of the porous microneedle arrays according to the present invention are drug delivery, i.e., delivery of active substances via the porous carrier zone and the porous microneedles into or under the skin, for example in a design as a patch containing active agents having an active agent reservoir to which microneedle array 4 is coupled.

Another application is blood glucose level determination via the transdermal fluid, which is drawn from beneath the surface of the skin by microneedles 4a, 4b, 4c, 4d and conveyed to a measuring system, for example in the form of a classic glucose test strip, which uses an enzyme such as glucose oxidase to selectively convert the glucose contained in the transdermal fluid to electricity for the purpose of measuring it; the current or the electric charge is thus evaluated as a measure of the glucose concentration.

Another example of an application are alcohol testers using the transdermal fluid, which is drawn from beneath the surface of the skin by microneedles 4a, 4b, 4c, 4d, and conveyed to a measuring system, for example in the form of a classic test strip, which uses an enzyme such as alcohol dehydrogenase to selectively convert the alcohol contained in the transdermal fluid to electricity for measuring purposes; the current or the electric charge is then evaluated as a measure of the alcohol concentration.

Although the present invention has been described above on the basis of preferred exemplary embodiments, it is not limited to these but is modifiable in many ways.

What is claimed is:

1. A porous microneedle array, comprising:
    a porous carrier zone formed at a face of a semiconductor substrate;
    plurality of microneedles disposed on a portion of the porous carrier zone between edge structures disposed on the face of the semiconductor substrate, wherein the edge structures vertically rise to above the plurality of microneedles; and
    a plastic cap positioned over the plurality of microneedles and covering the plurality of microneedles, wherein the plastic cap includes a surface extending continuously in a plane between flanges that interact with the edge structures for positioning the surface over the plurality of microneedles.

2. The porous microneedle array of claim 1, wherein the surface is a single planar surface that extends from a first of the flanges to a second of flanges.

3. The porous microneedle array of claim 2, wherein the surface is one of a plurality of surfaces which the plastic cap includes, each of the surfaces forming a single plane that extends from a respective first one of the flanges to a respective second one of the flanges and each of planar surfaces extending over a respective plurality of the microneedles.

4. A substrate composite, comprising:
    a plurality of porous microneedle arrays formed on a front face of a semiconductor substrate, each microneedle array including:
        a porous carrier zone; and
        a plurality of microneedles above a portion of the porous carrier zone and between edge structures that vertically rise from the carrier zone to above the plurality of microneedles; and
    a plastic cap substrate positioned over the microneedle arrays, wherein the plastic cap substrate includes a plurality of surfaces that each extends continuously in a single plane and that are separated from each other by flanges that interact with the edge structures for positioning respective ones of the surfaces over respective ones of the plurality of porous microneedle arrays, each of the arrays including more than one microneedle.

5. The substrate composite as recited in claim 4, wherein each microneedle array is laterally delimited by a respective pair of the vertically-rising edge structures.

6. The substrate composite as recited in claim 4, further comprising:
    an inter layer provided between the porous carrier zone and a non-porous residual layer of the semiconductor substrate located below the porous carrier zone, wherein the interlayer has greater porosity than the carrier zone.

7. The substrate composite as recited in claim 6, wherein the semiconductor substrate is a wafer substrate.

8. The substrate composition as recited in claim 4, wherein flanges of each of a plurality of pairs of a subset of the flanges are separated from each other by a respective recess into which a respective one of the edge structures is form-fittingly positioned.

9. The substrate composite as recited in claim 4, wherein each of the surfaces extends from a first respective one of the flanges to a second respective one of the flanges.

10. A porous microneedle array, comprising:
    a porous carrier zone formed at a face of a semiconductor substrate;
    plurality of microneedles disposed on a portion of the porous carrier zone between edge structures disposed on the face of the semiconductor substrate; and
    a plastic cap positioned over the plurality of microneedles and covering the plurality of microneedles;
    wherein:
        the edge structures vertically rise to above the plurality of microneedles;
        the plastic cap includes a substantially planar surface extending between flanges that interact with the edge structures for positioning the substantially planar surface over the plurality of microneedles; and
        an open space separates between the substantially planar surface and the plurality of microneedles over which the substantially planar surface is positioned.

* * * * *